United States Patent [19]

Coombs

[11] 4,003,834
[45] Jan. 18, 1977

[54] DENSITY GRADIENT FRACTIONATION BY PISTON DISPLACEMENT

[75] Inventor: David H. Coombs, Corvallis, Oreg.

[73] Assignee: The United States of America as represented by the Secretary of the Department of Health, Education and Welfare, Washington, D.C.

[22] Filed: Mar. 31, 1975

[21] Appl. No.: 563,513

[52] U.S. Cl. .................... 210/83; 23/259; 210/94; 210/516; 356/197; 356/244
[51] Int. Cl.² .......................... G01N 1/02
[58] Field of Search ......... 23/230 R, 253 R, 259 R; 73/325, 330, 334; 210/83, 92, 94, 511, 516, 518, DIG. 23; 302/58; 356/244, 246, 197

[56] References Cited

UNITED STATES PATENTS

| | | | |
|---|---|---|---|
| 1,681,339 | 8/1928 | Hall | 23/230 R |
| 3,178,266 | 4/1965 | Anthon | 23/253 R |
| 3,236,100 | 2/1966 | Benfield | 73/330 |
| 3,355,098 | 11/1967 | Farr | 210/DIG. 23 |
| 3,529,896 | 9/1970 | Padawer | 356/246 X |
| 3,617,222 | 11/1971 | Matte | 23/253 R X |
| 3,622,279 | 11/1971 | Moran | 23/230 R X |
| 3,682,305 | 8/1972 | Buchler | 23/253 R X |
| 3,712,746 | 1/1973 | Bergeron | 356/246 X |
| 3,759,667 | 9/1973 | Bannister et al. | 23/253 R X |
| 3,782,548 | 1/1974 | Bowen | 210/518 X |
| 3,918,913 | 11/1975 | Stevenson et al. | 23/259 R |

Primary Examiner—Frank A. Spear, Jr.
Assistant Examiner—R. G. Mukai
Attorney, Agent, or Firm—Browdy and Neimark

[57] ABSTRACT

A method and apparatus for the fractionation of centrifuged density gradients have been developed. The apparatus consists of a gradient holder composed of a transparent and an opaque section which contains an opening allowing a centrifuged tube containing a density gradient having individual bands to be inserted into the holder. A displaceable piston which is suspended above the holder and is connected to an actuator may be raised or lowered into the density gradient. A standard illuminating device is placed under the gradient holder so that the exact position of each individual band can be determined. Once the precise location is determined, the displaceable piston is lowered into the gradient and by operating the actuator, the desired band of gradient can be extracted. Additionally, this method may be utilized in a continuous fractionation of the entire gradient.

14 Claims, 7 Drawing Figures

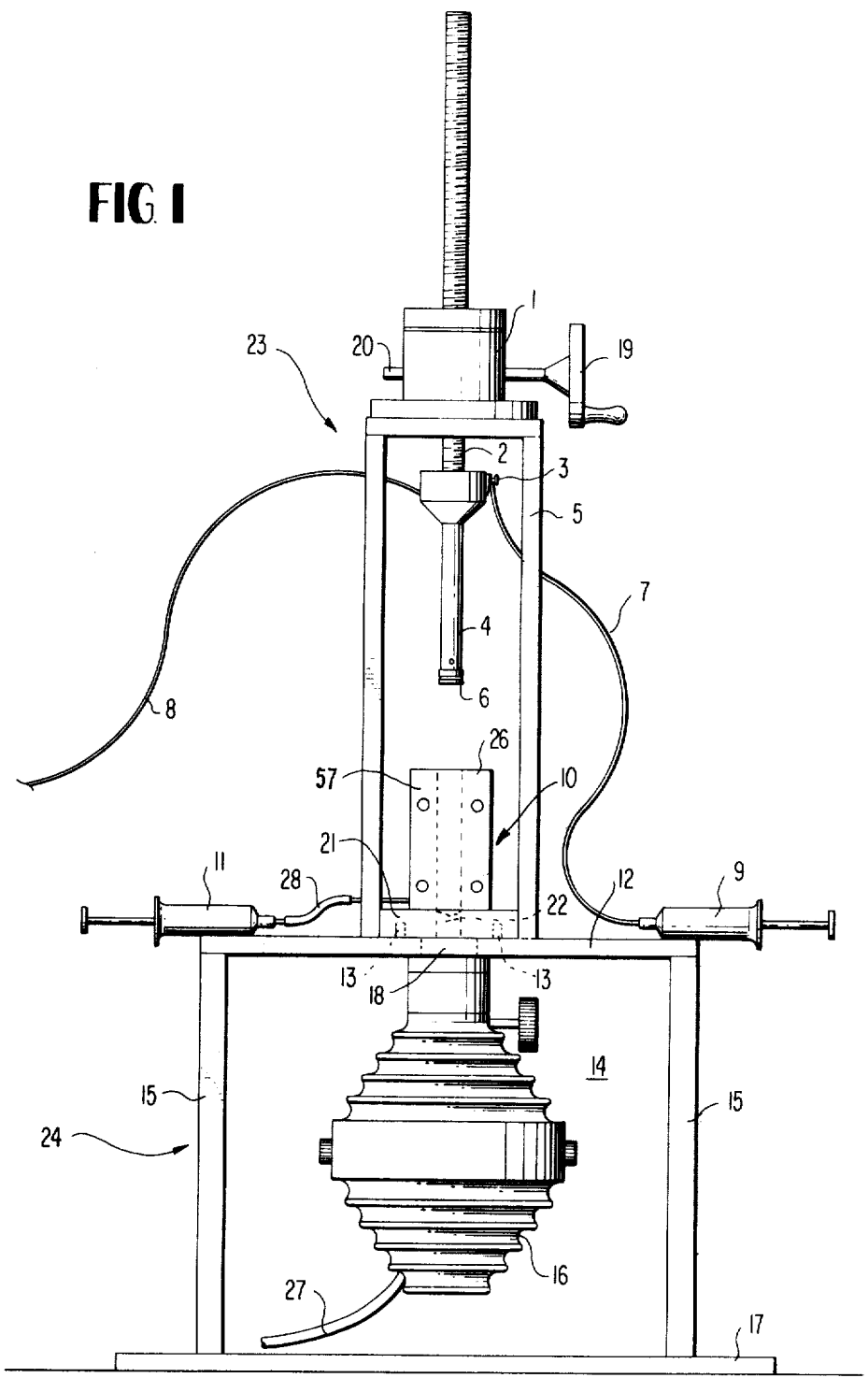

DENSITY GRADIENT FRACTIONATION BY PISTON DISPLACEMENT

FIELD OF THE INVENTION

This invention relates to a method and apparatus for fractionizing a density gradient after the gradient has been subjected to the centrifuge.

BACKGROUND OF THE INVENTION

Density gradient centrifugation is one of the most widely used separation methods in biochemical and biological sciences. Fractionation methods which have been developed usually involve displacement of the entire gradient either up or down in the centrifuge tube. One of the earliest and simplest of these methods of fractionation was one in which the bottom of the centrifuge tube is pierced with a fine needle and then the drops are collected. Recent improvements of this technique involve controlling the flow rate of the effluent or the speeds at which air or distilled water enters at the top of the centrifuge tube. A second common method of collection involves producing a dense solution at the bottom of the centrifuge tube and then allowing the gradient to flow up into an inverted collection funnel at the top.

These two fractionation techniques, however, share several disadvantages. First, vertical movement of the gradient causes contamination of some of the fractions of the gradient with particles being retarded near the wall. Furthermore, these methods also lack the important advantage of allowing isolation of individual bands made visible by scattered light, since such bands are lost from view as they near the collection point.

Two prior art methods which do permit the isolation of the individual bands include inserting a needle through the centrifuged tube just below the band, or lowering a capillary tube into the gradient until the open end lies just below the band. Both of these methods, however, can delute and contaminate the sample because collection is made from a single small opening, and is inadequate for isolating numerous bands from the same gradient.

SUMMARY OF THE INVENTION

In order to overcome the inadequacies of the prior art, a new fractionation device has been designed which operates in conjunction with a displaceable piston. According to this invention, the density gradient is fractionated from the top by displacement with a specially-tipped piston, which provides a rapid and precise isolation of visible bands without further movement of the gradient prior to fractionation. This instrument also permits rapid whole gradient fractionation in constant volume aliquots and allows the rinsing of the collection tubing before each band is removed. Furthermore, the centrifuge tubes can be reused thus reducing operational costs.

This method of fractionation has proven itself to be very useful and is a most valuable aid in the isolation of particles separable by density gradient centrifugation. The savings in time and material gained by extracting only the desired areas or bands from the gradient for electron microscopy, liquid scintillation or gel electrophoresis have been substantial. The only requirement for band-type fractionation is that the isolated structures be large enough (10–100 nm) to scatter visible light illuminated from a power source.

The fractionation apparatus contains a gradient holder which is constructed of one section composed of transparent material and a second section composed of an opaque material. After the density gradient has been suitably prepared, it is introduced into the gradient holder which is then positioned under a displaceable piston. This piston contains a collection tube at its end having a plurality of holes to enable the density gradient to flow into the piston and be carried away by a length of collection tubing. The displaceable piston is also connected to a rinsing syringe and can be connected to an air flow means such as a peristaltic pump so that the collection tubing can be cleansed with a buffer solution after the removal of each individual band or to allow for the continuous circulation of air during the collection process. Furthermore, this device permits individual band fractionation or whole gradient fractionation.

If individual band fractionation is desired, then an illuminating means below the gradient holder is actuated and the precise location of each individual band in the holder is noted. The displaceable piston is then loaded into the density gradient until the upper edge of the band is hidden. After a buffer solution is forced through a collection line, a piston is slowly lowered through the band until the entire band has been collected.

It is accordingly an object of the present invention to overcome the deficiencies in the prior art as mentioned above.

Another object is to provide improved fractionation.

Another object of the present invention is to produce a device which can efficiently fractionate a density gradient.

A further object of the present invention is to develop a fractionation device which precisely isolates a band of density gradient.

Yet another object of the present invention is to develop a fractionation device which utilizes a displaceable piston.

Still another object of the present invention is to develop a fractionation device which permits the rinsing of the collection tubing before and after each band is removed.

Another object of the present invention is to develop a fractionation device which visually detects the position of the individual bands of the gradient.

Another object of the invention is to develop a fractionation device which can collect a single band of density gradient without disturbing the other bands of the gradient.

BRIEF DESCRIPTION OF THE DRAWING

The above and additional objects and advantages inherent in the present invention will become more apparent by reference to the desription of an illustrative embodiment in a drawing thereof, in which:

FIG. 1 is a front view of a displaceable piston fractionation device in accordance with the present invention;

DETAILED DESCRIPTION OF THE PREFERRED EMBODIMENT

Figure 3:
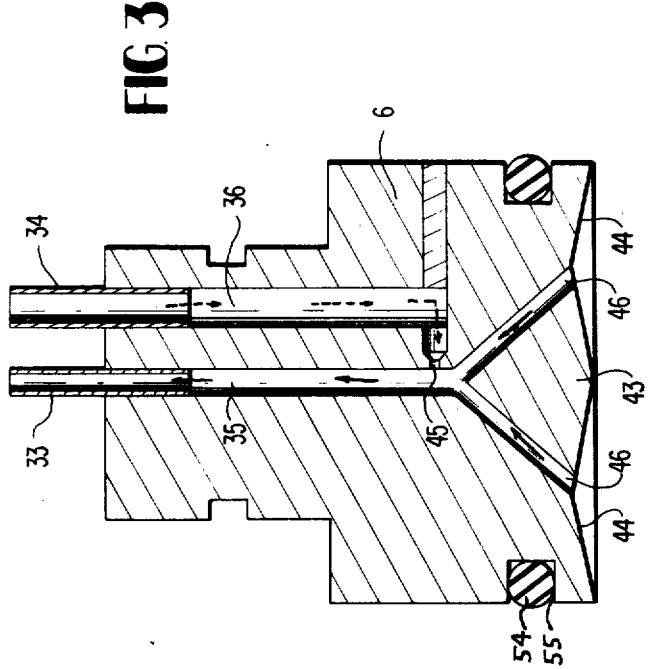
FIG. 3 is an axial cross section of the collection tip of the device of FIG. 1.

A displaceable piston fractionation device 23 in accordance with the present invention having a working stage 24 is most completely shown in FIG. 1. This working stage 24 serves as the housing for the apparatus and ensures that the working area will remain stable when the fractionation process is in progress. This working stage can be constructed of any strong durable material such as aluminum and contains a working stage top 12, a pair of support bars 15, a back support plate 14, and a base 17.

Figure 2:
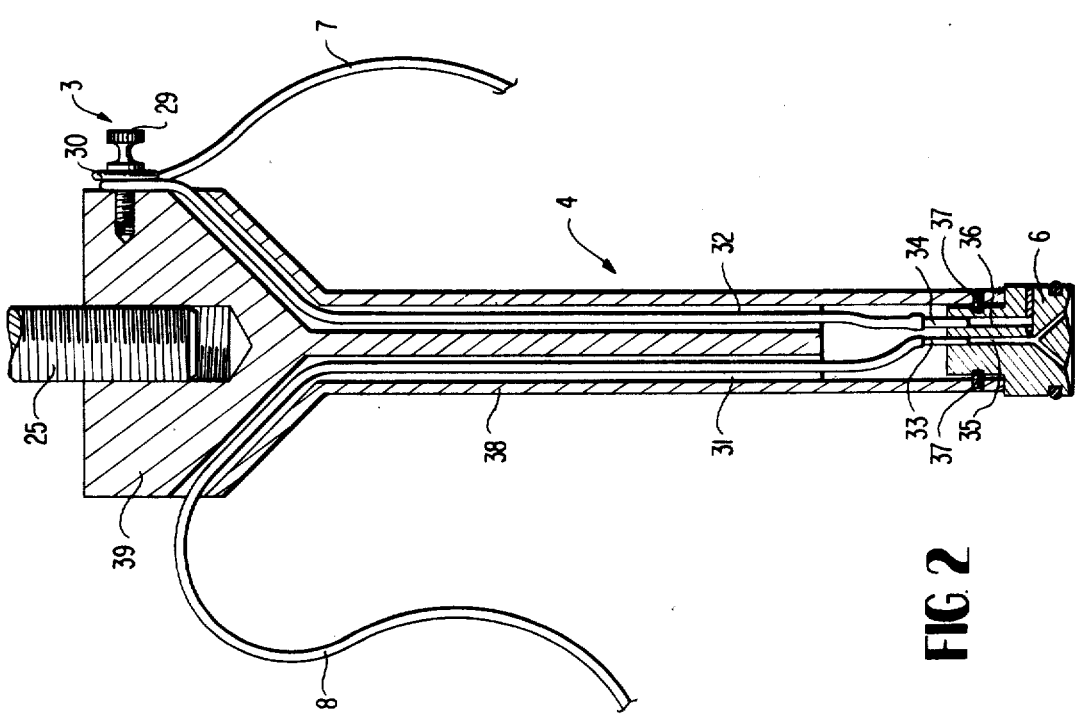
FIG. 2 is an axial cross section of the displaceable piston and collection tube device of FIG. 1.

A displaceable piston 4 is detachably connected to a threaded end 25 of a shaft 2 of a worm gear actuator 1. Any suitable actuator can be utilized with an actuator produced by the Duff-Norton Company (No. KT2554-6) being found to produce good results. The actuator 1 is fixed to an actuator support stand 5 which can be constructed of material similar to that of the working stage 24. As shown in FIG. 2, the piston 4 is connected to the shaft 2 of the actuator 1 by means of an inverted keyed lifting screw 25, threaded at the lower end. This particular actuator utilizes a handle 19, counterbalanced to prevent back action and is attached to one end of axle 20 connected to the actuator drive shaft 2 for manual operation. However, this is not the only means for operating the drive shaft, and a variable speed, reversible motor drive connected to the other end of the axle 20 could just as easily be used.

A gradient holder 10 comprising a holder base 21 and a holder top 26 is affixed to the working stage top 12 of the working stage 24 by two alignment pins 13 attached to the gradient holder base 21. These alignment pins 13 fit into holes 56 (FIG. 6) in the gradient holder base 21 and ensure that the gradient holder 10 will remain steady and properly aligned when the density gradient is being extracted.

An illumination means 16 is placed under the working stage top 12 and is aligned with the gradient holder 10 so that when the illumination source is activated by flipping a switch located on the illuminator power cord 27, the individual bands of the density gradient can be precisely located. While any standard illumination source can be utilized for this purpose, the detection of very faint minor bands being desired, a powerful light source such as produced by the American Optical Company (No. 735) was found to give good results. A light hole 18 is provided in the working stage top 12 to enable a beam of light to pass through and illuminate the density gradient. To protect the untempered lens of the light system from accidental spills, an optically clear, glass petri dish cover is placed over the lens.

Figure 4:
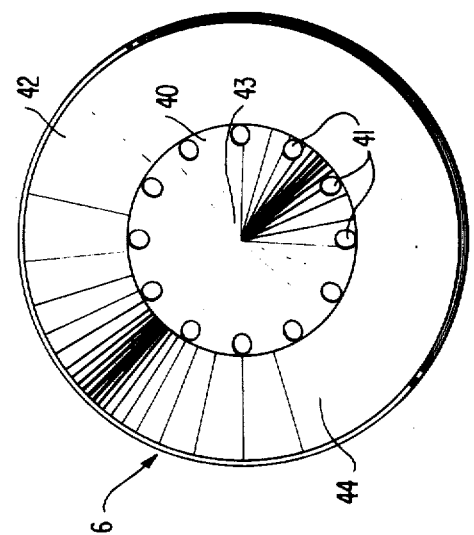
FIG. 4 is a bottom view of the collection tip of FIG. 3.

The displaceable piston 4 and its collection tip 6 are most clearly shown in FIGS. 2, 3 and 4. The piston 4 consists primarily of a substantially cylindrical body 38 and an enlarged head 39 which is connected to the actuator shaft 2 via the threaded lifting screw 25. The piston contains two angled channels 31 and 32 into which a collection tubing 8 and rinse tubing 7 are threaded. The collection tubing 8 and rinse tubing 7 are connected to leads 33 and 34 respectively, which are disposed in their respective channels 35 and 36 in the tube tip 6. The opposite end from connecting lead 33 of the collecting tube 8 can be connected to any standard reception device for accumulation of density gradients.

The end of the rinse tubing 7 opposite from lead 34 is connected to a rinse syringe 9 which rests on the working stage top 12. This syringe contains any suitable type of buffer solution for rinsing and cleansing the collection tubing before and after the withdrawal of each individual band. The tubing 7 passes through a tubing clamp mechanism 3 consisting of a tubing clamp 29 and a washer 30. Therefore, when a buffer solution is desired to be introduced into the piston 4 and piston tip 6, the tubing clamp is loosened and the solution is allowed to flow. This clamp 29 can then be tightened when the flow of buffer solution is no longer needed.

The tip 6 is provided with a pair of set screws 37 which hold the tip in place with respect to the piston 4 during the operation of this device. These set screws also allow the tip 6 to be removed from the piston 4. This is important since the piston can now accept interchangeable collection tips for the various size centrifuge tubes utilized in the laboratory, thus minimizing cost. The length and diameter of the body portion 38 was designed so that it could be used in conjunction with the longest and narrowest centrifuge tubes in operation.

FIGS. 3 and 4 show the collection tip 6 in great detail. Although different designs of the tube tip could be used, it was found that a tip having a conical collection face 43 cut at a 10° angle from the horizontal and containing approximately 12 radially spaced collecting holes 41 placed in a circular, ∧-shaped groove 40 produced excellent results in collecting just the desired band of gradient and not disturbing any adjacent bands.

A malleable silicone "O" ring 54 which has the same cross-sectional thickness in its final stretched position as the width of the O ring groove 55 is provided. Thus, when the tip 6 is inserted into a centrifuge tube, the compressed O ring fills the entire groove, preventing entrapment of upper parts of the gradient and their possible subsequent release. Since glare should be reduced to a minimum, this tip 6 as well as the piston 4 and the working stage 24 should be constructed of black anodized aluminum.

This particular configuration allows the volume of the entire collection system to be kept to approximately 0.1 ml by utilizing a collection hole diameter of 0.020 inches and an effluent tubing inside diameter of 0.023 inches. However, it can be appreciated that other collection volumes may be utilized.

The design of the tip 6 is important since the gradient itself is immobile in the centrifuge tube and when the piston is then made immobile after it has been lowered into the gradient, no unwanted portion of the gradient can flow to the collection tubing 8 as, for instance, during rinsing. This configuration is also aided by the presence of angular surface 44 which extends from the groove 40 to the outer surface 42 of the collection tip. This section is cut at a 10° angle from the horizontal but in the opposite direction than the conical section 43.

FIG. 3 shows an enlargement of the collection tip 6 and also indicates the direction of flow of the gradient during the collection process and of the rinsing buffer solution. The path of the fractionated liquid is shown in the solid arrows and the path of the rinse solution is shown by the broken arrows. Once the rinse solution flows into channel 36, it is introduced into the collection system through an "L"-shape hole 45 in the collection tip 6. Since the actuator 1 holds the piston 4 firmly in place, the rinse solution travels up the collection tubing 8 and not down into the gradient through flow channels 46. These flow channels 46 (two of which are shown in FIG. 3) allow the gradient to enter into channel 35 and thereby proceed into the collection tubing 8.

Any standard type rinse and collection tubing such as Intradmedic PE 200 or PE 50 can be connected to the collection tip 6 with a 19 gauge and 22 gauge stainless steel tube respectively, and threaded through the proper channels in the piston shaft. The section of the rinse tubing 7 which is clamped, should be heat-flattened to prolong life.

Figure 5:
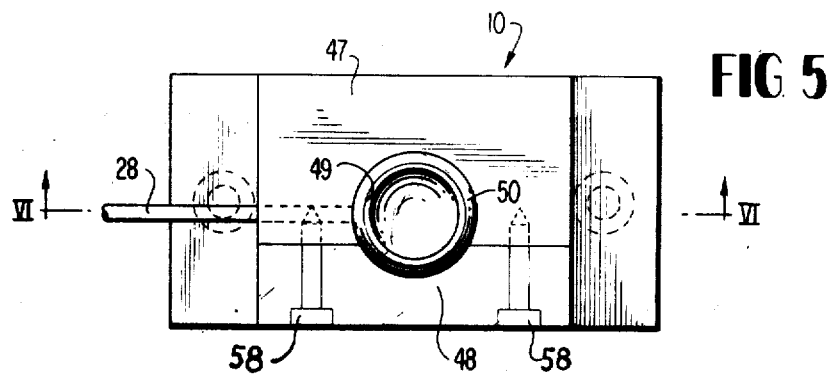
FIG. 5 is a top view of the gradient holder of the device of FIG. 1.
Figure 6:
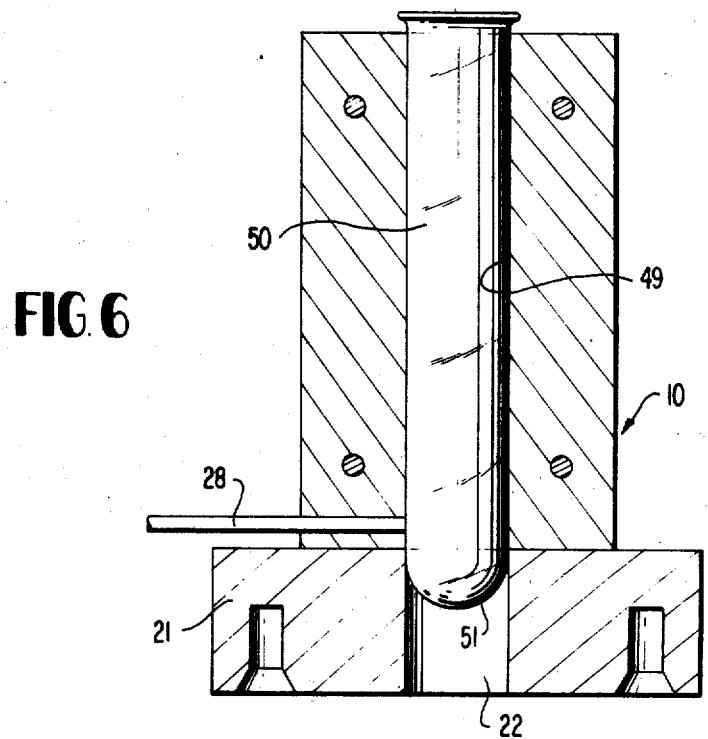
FIG. 6 is a cross section of the gradient holder taken along line VI—VI of FIG. 5.

The gradient holders which are used in this apparatus were designed to optimize band visibility while holding the tubes firmly during fractionation, and are best depicted in FIGS. 5 and 6. The laminated holder top is made of two substantially rectangular sections 47 and 48. Section 48 is situated in the foreground of the gradient holder 10 and should be constructed of a transparent material such as Plexiglas. The second section of the gradient holder top 47 should be constructed of a black Plexiglas material and is used to produce a dark background for the density gradient. A centrifuge tube hole 49 is drilled near the interface of these two sections so that approximately ¾ of the circumference of the hole lies in the black Plexiglas section 47 and about ¼ of the circumference lies in the transparent plastic section 48. Screws 58 are provided to reinforce the bonded transparent plastic 48 and the black Plexiglas 47 sections. The polished transparent surface thus provides the window for the gradient, otherwise surrounded in black.

A transparent plug 22 having an upper concave surface 51 matching the curvature of the bottom end of the cellulose nitrate centrifuge tube, is inserted into the base 21 of the gradient holder for tube support and illumination. This concave surface 51 counteracts the lens effect of the bottom of the centrifuge tube, thereby allowing parallel illumination over the length of the gradient, thus ensuring a proper illumination of all of the individual bands appearing in the gradient.

Stainless steel tubing 28 is inserted into the holder 10 just above the transparent plug 22 and is connected to a syringe 11 which rests on the working stage top 12. This syringe contains a solution of glycerol or mineral oil which would fill the narrow gap between the tube and the gradient holder 10 with a medium having a high reflective index, thus improving band visibility by eliminating surface reflections. Since there must be a relatively snug fit between the centrifuge tube and the holder 10, different holders corresponding to the different centrifuge tubes in laboratory operation have been developed.

Figure 7:
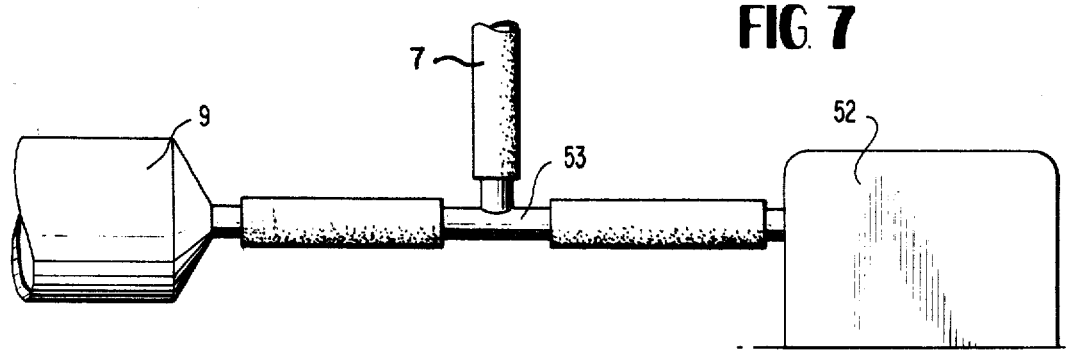
FIG. 7 is another embodiment of the present invention showing the connection of the rinse tubing to an air pump.

Another embodiment of the invention is shown in FIG. 7 which shows the rinse syringe and a peristaltic pump 52 connected to the rinse tubing 7 through a "T" valve 53. In this manner, air which is pumped from the peristaltic pump 52 can be used instead of the buffer solution to better define the different bands in the density gradient when they have been displaced from the gradient holder 10 or which can be used in whole-gradient fractionation.

The above described invention operates in the following manner. The rinse tubing 7 and the collection tubing 8 are connected to the collection tip 6 and are threaded through their proper channels in the piston body 36. The syringe 9, filled with a standard buffer solution, is connected to the rinse tubing 7 and the line is filled before it is clamped. Approximately ¾ of the gradient holder volume (the volume of centrifuge hole 49) is filled with a 70% glycerol or light oil solution using the large syringe 11 connected to stainless steel tubing 28. When a centrifuge tube is placed into the holder, it pushes the solution back through the stainless steel tubing 28 into the syringe 11. The film of glycerol or oil between the tube and the holder 10 reduces the glare. The centrifuge tubes must be pretested for holder fit and must have the sharp inner edge of the rim scraped off to prevent damage to the O ring 54. Light lubrication of the O ring is advised. If air bubbles persist on the face once the piston has entered the gradient, they can usually be removed by sharply rotating the actuating handle 19 one revolution downwards. Further, persistent bubbles can be prevented by pre-cleaning the conical face 43 with acetone.

Whole gradient fractionation in constant volume aliquots can be accomplished utilizing this invention by lowering the piston shaft 38 into the density gradient and discontinuously operating the handle 19. The volume displaced employing this method is determined by the diameter of the gradient and the fraction, or number of turns per sample. (In this particular configuration one turn of the handle moves the piston 1.25 mm).

If, however, isolation of individual bands is desired, the illuminating means 16 is switched on and the exact position of each individual band is marked on a tape 57 applied next to the gradient, and then the piston 4 is carefully lowered until the upper edge of the band is just hidden. The rinse clamp 3 is now loosened and a buffer solution is forced through the collection line 8, and when the clamp 3 is retightened the piston 4 is slowly lowered through the band. The first 0.1 ml (residual rinse solution) is discarded and the effluent is collected until the piston 4 has displaced the entire band. After each band has been displaced, the clamp 3 is then again loosened and more buffer solution is forced through the collection tube 8 to force out desired liquid from the collection system. When the fractionation is completed, the piston 4 is raised and the tube is removed from the gradient holder. A rinse of distilled water and acetone following use of the fractionator will prevent growth of algae in the tubing.

It has been determined, however, that whenever a gradient is transported in any length of tubing, the laminar capillary flow in the collection line reduces the resolution achieved on the gradient. The loss of the resolution increases in high viscosity sucrose solutions which are often used in gradient work. While this problem is largely eliminated in the piston design by rinsing before each individual band is removed, it decreases resolution when continuous fractionation is attempted.

It has been discovered that if air rather than a buffer solution is continuously pumped into the rinse line during the fractionation, the effluent from the gradient is compartmentalized by air spaces during its passage through the tubing. Laminar capillary flow is eliminated and the only cross-contamination possible is by the small volume of liquid which adheres to the wall in the air space between each liquid segment. This method is already in use in clinical hospital analyzers where samples separated by air spaces travel over large lengths of tubing. This concept can easily be adapted to piston displacement fractionation. If continuous fractionation is desired, a peristaltic pump 52 can be connected to the rinse tubing which can continuously circulate air during the collection process. The operator can then crank the actuator for one or more revolutions, and then pause while the air drives the remainder of the fraction from the tubing. This process can be repeated for each successive fraction. Alternatively, air bubbles which are mixed with the fraction could be eliminated by clamping the air line during cranking and then driving the remaining liquid out with a small burst of air between each fraction.

Extracting individual bands with the piston fractionator is facilitated because the rinse and sample can be prevented from mixing by separating them from air. In this situation, the operator can crank down to a position just above the band with the rinse clamp closed. The rinse clamp is then loosened and a buffer is forced through the tubing as usual. A T valve on the rinse line is switched from buffer to air, and the rinse itself is removed from the collection tubing. With the air still entering, the piston is cranked through the band in question until it has been completely removed from the gradient. The operator then pauses to collect the last few drops as they are carried out from the tubing by air, closes the clamp, and cranks down to the next band where he repeats this procedure.

It will be obvious to those skilled in the art that various changes may be made without departing from the scope of the invention and the invention is not to be considered limited to what is shown in the drawings and described in the specification. For example, the particular design of the gradient holder which has been described is not to be construed to be limited in use to gradient densities. This holder can have various applications in the photography of gradients which is incidental to its function on the fractionation device.

I claim:

1. A fractionation apparatus for the fractionation of a density gradient of liquids comprising:
   a gradient holder having a centrifuge tube hole for receiving a centrifuge tube containing a density gradient of liquids having individual bands;
   a black, rigid displaceable piston of external diameter equal to the internal diameter of the centrifuge tube suspended above said holder, said piston having at least one opening passing therethrough and having sealing means thereabout to prevent liquid from escaping by the piston when it is displaced within the tube;
   a collection means connected to said displaceable piston for collecting the density gradient through said opening;
   actuator means connected to said displaceable piston for incrementally and accurately lowering said piston into and for raising said piston from the density gradient within the centrifuge tube; and
   illuminating means placed under said gradient holder for illumination of the density gradient to determine the exact position of each individual band.

2. A fractionation apparatus according to claim 1 further including a rinse means connected to said displaceable piston for cleaning said collection means.

3. A fractionation apparatus according to claim 2 wherein said rinse means contains a buffer solution for cleaning said collection means before and after each individual band of gradient is removed.

4. A fractionation apparatus according to claim 2 wherein said rinse means contains an air pump for constantly passing air through said collection means.

5. A gradient holder containing a hole comprising:
   a first vertically extending section composed of transparent material;
   a second vertically extending section composed of opaque material and lying horizontally adjacent said first section;
   said first and second sections defining therebetween said hole at the interface of said first and second sections with the majority of the circumference of said hole lying in said second section, and a transparent plug connected to the bottom of said gradient holder at the bottom of said first and second sections;
   and illuminating means beneath said transparent plug.

6. A displaceable piston in a fractionation apparatus comprising:
   a rigid piston body;
   a collection tip connected to one end of said piston, said collection tip having an inverted V-shaped groove at its outer end, and containing a plurality of collecting holes in said groove; and
   collection means connected to the collecting holes of said collection tip and passing through said piston body for collecting the density gradient.

7. A displaceable piston according to claim 6 further including a rinse means connected to said piston body for cleaning said collection means without disturbing unfractionated gradient.

8. A method for density gradient fractionation comprising the steps of:
   preparing in a container a density gradient having individual bands;
   inserting said container with said density gradient into a density gradient holder;
   illuminating said density gradient holder thereby locating the precise location of each individual band;
   lowering a rigid displaceable piston of external diameter equal to the internal diameter of said container and having a collection tip into the density gradient in the container in the gradient holder;
   collectng at least a portion of said density gradient by forcing said portion through said collection tip due to the lowering of said piston;
   removing said displaceable piston from said gradient holder; and
   rinsing said displaceable piston with buffer solution before and after the removal of a portion of the density gradient with a selected quantity of said buffer solution, the flow of buffer being stopped to prevent flow during fractionation.

9. A method for density gradient fractionation according to claim 8 further including:
   marking the precise location of each individual band on said gradient holder before lowering said displaceable piston into said gradient holder.

10. A method for density fractionation according to claim 9 comprising the step of:
    adding a solution of glycerol or mineral oil or other suitable medium to said gradient holder before said density gradient is inserted into said density gradient holder, wherein glare is eliminated and the visibility of the bands in the gradient is enhanced.

11. A method for density gradient fractionation according to claim 8 further comprising the step of:
    circulating air through said displaceable piston during the removal of the density gradient.

12. A fractionation apparatus for the fractionation of a density gradient of liquids comprising:

a gradient holder having a centrifuge tube hole for receiving a centrifuge tube containing a density gradient of liquids having individual bands, said density gradient holder comprising first and second vertically extending sections placed horizontally adjacent one another, said first section being composed of a transparent material, and said second section being composed of an opaque, black material, said first and second sections defining therebetween said tube hole at their interface with the majority of the circumference of the tube hole lying in said second section;

a rigid displaceable piston of external diameter equal to the internal diameter of the centrifuge tube suspended above said holder, said piston having at least one opening passing therethrough;

collection means connected to said displaceable piston for collecting the density gradient through said opening;

actuator means connected to said displaceable piston for incrementally and accurately lowering said piston into and for raising said piston from the density gradient within the centrifuge tube; and illuminating means placed under said gradient holder for illumination of the density gradient to determine the exact position of each individual band.

13. A fractionation apparatus according to claim 12 further including a transparent plug connected to the bottom of said gradient holder for supporting and permitting illumination of said centrifuge tube.

14. A fractionation apparatus for the fractionation of a density gradient of liquids comprising:

a gradient holder having a centrifuge tube hole for receiving a centrifuge tube containing a density gradient of liquids having individual bands;

a rigid displaceable piston of external diameter equal to the internal diameter of the centrifuge tube suspended above said holder, and collection means connected to said displaceable piston for collecting the density gradient, said collection means containing a collection tip connected to the end of said displaceable piston, said tip having an inverted V-shaped groove on its outer end, and containing a plurality of collecting holes in said groove, said piston having an O-ring on its outer edge to prevent liquid from escaping at the side of the piston when the piston is displaced, whereby liquid passes through said collecting holes;

actuator means connected to said displaceable piston for incrementally and accurately lowering said piston into and for raising said piston from the density gradient within the centrifuge tube; and illuminating means placed under said gradient holder for illumination of the density gradient to determine the exact position of each individual band.

* * * * *